US012806443B2

(12) United States Patent
Carlsson

(10) Patent No.: US 12,806,443 B2
(45) Date of Patent: Nov. 24, 2026

(54) METHOD FOR USE WITH A RADIOTHERAPY DEVICE

(71) Applicant: Elekta Limited, Crawley (GB)

(72) Inventor: Per Carlsson, Crawley (GB)

(73) Assignee: Elekta Limited, Crawley (GB)

( * ) Notice: Subject to any disclaimer, the term of this patent is extended or adjusted under 35 U.S.C. 154(b) by 270 days.

(21) Appl. No.: 18/696,313

(22) PCT Filed: Oct. 21, 2022

(86) PCT No.: PCT/EP2022/079486
§ 371 (c)(1),
(2) Date: Mar. 27, 2024

(87) PCT Pub. No.: WO2023/067195
PCT Pub. Date: Apr. 27, 2023

(65) Prior Publication Data
US 2026/0131161 A1 May 14, 2026

(30) Foreign Application Priority Data
Oct. 22, 2021 (GB) ...................................... 2115213

(51) Int. Cl.
*A61N 5/10* (2006.01)

(52) U.S. Cl.
CPC ......... *A61N 5/1036* (2013.01); *A61N 5/1047* (2013.01); *A61N 5/1049* (2013.01); *A61N 2005/1061* (2013.01)

(58) Field of Classification Search
CPC .. A61N 5/1036; A61N 5/1047; A61N 5/1049; A61N 2005/1061
See application file for complete search history.

(56) References Cited

U.S. PATENT DOCUMENTS 5,818,902 A 10/1998 Yu
6,449,335 B1 9/2002 Siochi
(Continued)

FOREIGN PATENT DOCUMENTS

WO WO 2007124760 A1 * 11/2007 ............. A61N 5/103
WO WO-2009050615 A1 4/2009
(Continued)

OTHER PUBLICATIONS

"British Application Serial No. 2115213.7, Examination Report dated Jan. 22, 2024", (Jan. 22, 2024), 3 pgs.
(Continued)

*Primary Examiner* — Uzma Alam
*Assistant Examiner* — Richard O Toohey
(74) *Attorney, Agent, or Firm* — Schwegman Lundberg & Woessner, P.A.

(57) ABSTRACT

Disclosed herein is a method of producing an irradiation sequence for a radiotherapy device to deliver radiation according to a treatment plan. The radiotherapy device comprises a rotation gantry, a radiation source coupled to the rotation gantry for rotation through arc segments, and a multi-leaf collimator comprising a plurality of moveable leaves. The multi-leaf collimator is configured to delimit radiation from the radiation source by controlling the position of each of the moveable leaves. The method comprises receiving a treatment plan comprising, for each of a plurality of arc-segments, a set of leaf positions comprising a position for each of the plurality of moveable leaves; and ordering the plurality of arc-segments into an irradiation sequence based on the sets of leaf positions, wherein the irradiation sequence, when executed by a radiotherapy device, delivers radiation according to the treatment plan.

14 Claims, 7 Drawing Sheets

(56) References Cited

U.S. PATENT DOCUMENTS

| | | | | |
|---|---|---|---|---|
| 2013/0077751 | A1 | 3/2013 | Gunawardena et al. | |
| 2022/0118286 | A1* | 4/2022 | Landrith .............. | A61N 5/1045 |
| 2022/0219013 | A1* | 7/2022 | Andersson ........... | A61N 5/1047 |
| 2024/0198134 | A1* | 6/2024 | Smith .................. | A61N 5/1048 |

FOREIGN PATENT DOCUMENTS

| | | | | |
|---|---|---|---|---|
| WO | WVO-2018031365 | A1 | 2/2018 | |
| WO | WO 2018050886 | A1 * | 3/2018 | ............. A61N 5/103 |
| WO | WO-2019210456 | A1 | 11/2019 | |

OTHER PUBLICATIONS

"British Application Serial No. 2115213.7, Examination Report dated Mar. 4, 2022", (Mar. 4, 2022), 5 pgs.
"International Application Serial No. PCT/EP2022/079486, International Search Report dated Feb. 17, 2023", (Feb. 17, 2023), 5 pgs.
"International Application Serial No. PCT/EP2022/079486, Written Opinion dated Feb. 17, 2023", (Feb. 17, 2023), 7 pgs.

* cited by examiner

METHOD FOR USE WITH A RADIOTHERAPY DEVICE

PRIORITY APPLICATIONS

This application is a U.S. National Stage Filing under 35 U.S.C. § 371 from International Application No. PCT/EP2022/079486, filed on Oct. 21, 2022, and published as WO/2023067195 on Apr. 27, 2023, which claims the benefit of priority to British Application No. 2115213.7, filed on Oct. 22, 2021; the benefit of priority of each of which is hereby claimed herein, and which applications and publication are hereby incorporated herein by reference in their entireties.

FIELD OF INVENTION

This disclosure relates generally to the delivery of radiotherapy, and in particular to planning and controlling the delivery of radiation or radiotherapy.

BACKGROUND

Radiotherapy involves the production of a beam of ionising radiation, usually X-rays or a beam of electrons or other sub-atomic particles. This is directed towards a cancerous region of a patient, and adversely affects the tumour cells causing an alleviation of the patient's symptoms. The beam is delimited so that the radiation dose is maximised in the tumour cells and minimised in healthy cells of the patient, as this improves the efficiency of treatment and reduces the side effects suffered by a patient.

In a radiotherapy apparatus the beam can be delimited using a beam limiting device such as a 'multi-leaf collimator' (MLC). This is a collimator which consists of a large number of elongate thin leaves arranged side to side in an array. Each leaf is moveable longitudinally so that its tip can be extended into or withdrawn from the radiation field. The array of leaf tips can thus be positioned so as to define a variable edge to the collimator.

All the leaves can be withdrawn to open the radiation field, or all the leaves can be extended so as to close the radiation field. Alternatively, some leaves can be withdrawn and some extended so as to define any desired shape, within operational limits. A multi-leaf collimator usually consists of two banks of such arrays, each bank projecting into the radiation field from opposite sides of the collimator.

A treatment procedure typically comprises irradiating the patient from multiple angles around an axis of rotation coinciding with the location of the cancerous region. In this way, the cancerous region can be targeted for longer while spreading out the radiation dose to healthy tissue surrounding the cancerous region. As the angle of radiation changes, the beam limiting device adjusts the beam shape by adjusting leaf positions in order to protect vulnerable tissue and to limit the beam to the shape of the cancerous region. Moving bulky equipment (typically several metres in diameter), including the radiation source and the many elongate leaves of the MLC, with a high degree of precision is a slow process. This puts a critical limitation on the time it takes for each patient to be treated, adversely affecting both patient welfare and the number of patients that can be treated per machine per day.

The present disclosure seeks to address these and other disadvantages encountered in the prior art by providing irradiation sequences and methods of delivering said irradiation sequences which minimize patient treatment time.

SUMMARY

An invention is set out in the independent claims. Optional features are set out in the dependent claims.

BRIEF DESCRIPTION OF FIGURES

Specific embodiments are now described, by way of example only, with reference to the accompanying drawings, in which.

DETAILED DESCRIPTION

In the following, a method, apparatus and computer-readable medium for reducing treatment delivery time are provided. The apparatus may be configured to perform any of the method steps presently disclosed and may comprise computer executable instructions which, when executed by a processor, cause a processor to perform any of the method steps presently disclosed. Any of the steps that the apparatus is configured to perform may be considered as method steps of the present disclosure and may be embodied in computer executable instructions for execution by a processor.

Application of radiotherapy to a patient will be referred to in more detail in order to provide clarity of explanation. Such use of the term patient should not be interpreted to limit application of the present disclosure. The present disclosure provides means that can be used to apply radiotherapy to any subject. The terms patient and subject may be used interchangeably herein.

Figure 1:
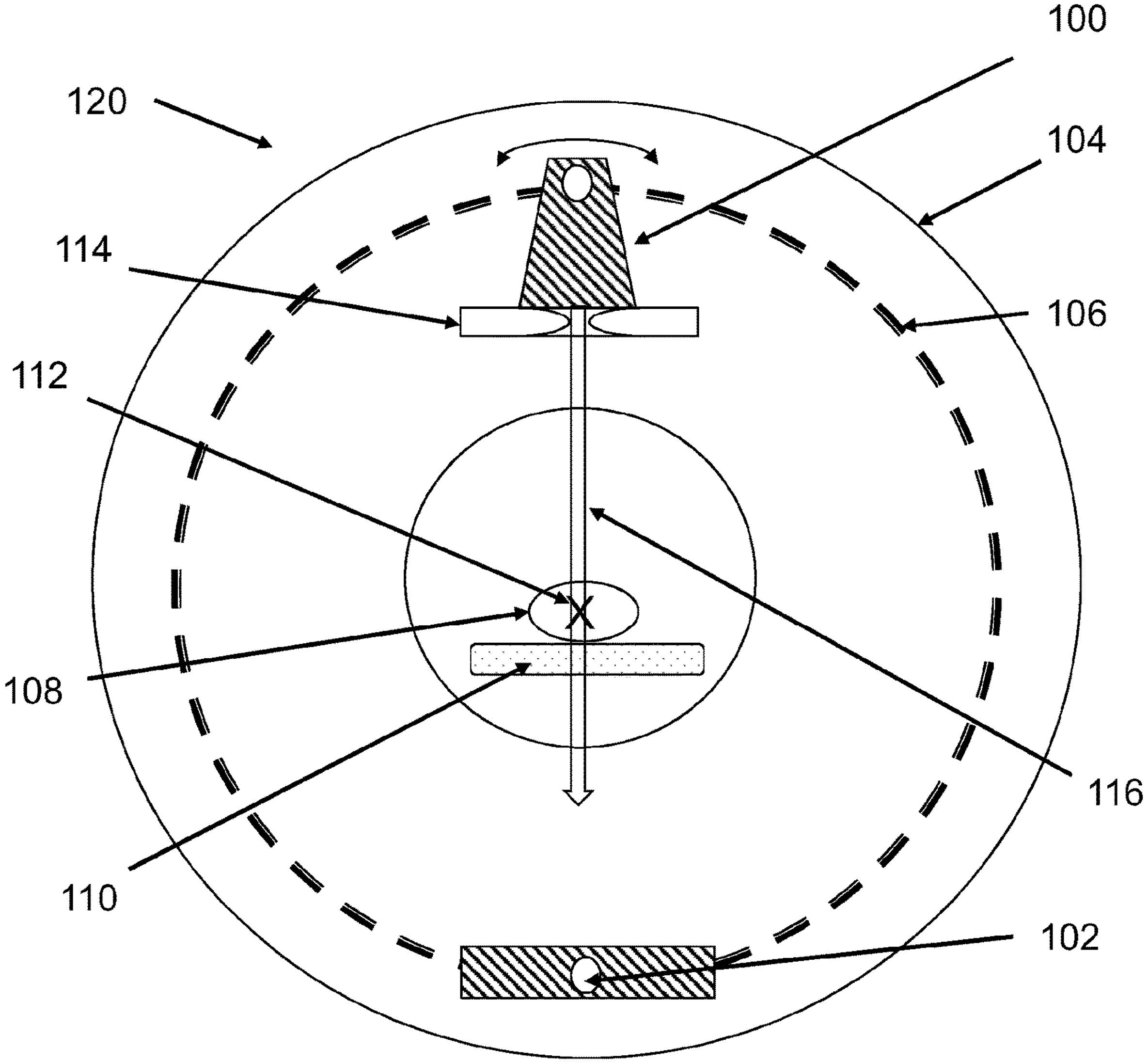
FIG. 1 depicts a schematic illustration of a radiotherapy device.

FIG. 1 depicts a radiotherapy device according to the present disclosure. The arrangement described should be considered as providing one or more examples of a radiotherapy device 120 and it will be understood that other arrangements are possible and can be used to perform the methods described herein. The figure shows a cross-section through a radiotherapy device 120 comprising a radiation source 100 and a detector 102 attached to a gantry 104. The radiation source 100 and the detector 102 rotate with the gantry. The radiation source 100 and the detector 102 may be arranged diametrically opposed to one another.

FIG. 1 also depicts a subject 108 on a support surface 110. The support surface 110 may be moved longitudinally relative to the gantry 104 for example to aid positioning of the subject 108. As radiation is applied to the subject 108, for example according to a treatment plan, the radiation source 100 rotates with the gantry 104. The radiation source 100 directs radiation towards the subject 108 from various angles around the subject 108 in order to spread out the radiation dose received by healthy tissue to a larger region of healthy tissue while building up a prescribed dose of radiation at a target region. As shown in FIG. 1*a*, radiation may be emitted in a plane which is perpendicular to the axis of rotation of the radiation source 100. Thus, radiation may be applied to a radiation isocentre 112 at the centre of the gantry 104 regardless of the angle to which the radiation source 100 is rotated around the gantry 104.

The spatial distribution of the application of radiation may be adjusted using a beam limiting device, for example a multi-leaf collimator (MLC) 114, arranged in a path of a radiation beam emitted by the radiation source 100. The MLC comprises a plurality of moveable leaves and the MLC is configured to delimit radiation from the radiation source 100 by controlling the position of each of the moveable leaves.

As explained above, in radiotherapy, radiation is directed towards a cancerous region of a patient (e.g. a tumour). A treatment plan is provided which outlines the correct dose of radiation to be delivered the patient, to target the target cells whilst minimising the dose to adjacent healthy cells.

The amount of radiation required to be delivered to a patient in a treatment session is entered into a planning computer in the form of a desired dose distribution. A planning computer may include a treatment planning computer and a delivery planning computer. Alternatively, the treatment planning computer and the delivery planning computer may be separate entities referred to collectively as a planning computer.

The treatment planning computer receives the dose distribution. The treatment planning computer determines a treatment plan by calculating the necessary rotations, dose rates (dose is plotted against the movement axes, so it is the speed of a movement that actually defines the dose rate where the amount of dose to be delivered over a particular distance has been defined), and collimator shape for the delivery of the dose distribution to a patient.

The amount of radiation required to be delivered to a patient in a treatment session is determined in the form of a desired dose distribution. The dose distribution includes a three-dimensional map showing areas which must receive a specified dose of radiation, such as the lesion itself, areas in which the dose should be minimised to the extent possible, and areas where substantially no radiation or less than a specified dose must be delivered, such as sensitive structures and vital organs.

A treatment planning computer determines a treatment plan by calculating the necessary gantry rotations, dose rates and multi-leaf collimator shape for the delivery of the dose distribution to a patient. The treatment planning computer creates a desired treatment plan in terms of a sequence of control points. Each "control point" defines a position/angle of the gantry, the dose that is to be delivered between this and the next (or previous) control point, and the shape of the MLC at that control point. Control points could (in theory) be spaced strategically around the complete arc. However, the availability of relatively cheap processing power means that there is little benefit in going to the effort of doing so, and control points are therefore typically spaced regularly around the arc such as every degree, every few degrees, or every fraction of a degree.

This treatment is put into effect by, between the nth and the (n+1)th or contiguous control points, moving the gantry from the position of the nth control point to the position of the (n+1)th control point at a rotation velocity and a dose rate that combine to deliver the required dose, while moving the MLC leaves so that when the gantry is at the (n+1)th control point, the leaves are in the correct position for that point. Typically, the MLC leaves will be moved at a rate which ensures that at all times their distance moved is linearly related to the dose that has been delivered in the arc-segment. This process is then repeated for the arc-segment between the (n+1)th and the (n+2)th control points, and so on until the treatment is complete.

An arc-segment is defined as a range of gantry angles, for example a first arc-segment may be defined by a gantry angle range 0-1° or any other angular range which may be constant or varying Equivalently or alternatively, an arc-segment may be defined by two or more control points, for example the first arc-segment may be defined by a first and second control point which can be consecutive or non-consecutive. A control point comprises a gantry angle it relates to (along with other information), for example, a first control point may be defined by a gantry angle 0° and a second control point may be defined by a gantry angle 1°.

In some examples, treatment delivery comprises rotation of the radiation source 100 through a predetermined angle and application of radiation by the radiation source 100, for example according to the treatment plan. The radiation source 100 may rotate in a series of continuous or substantially continuous arc-segments. In other examples, the gantry may rotate to and pause at a plurality of discrete angles.

As described above, as the angle of radiation changes, the shape of the beam is adjusted to match the shape of the tumour according to the control points of the treatment plan. Individual leaves of the MLC are driven to move into the positions specified by the treatment plan, and the movement of the MLC leaves occurs simultaneously with movement of the rotation source 100 on the rotation gantry 104. When the gantry angle in the treatment plan is reached, the MLC leaves are required to be ready in the correct positions in order to shape the beam to the shape of the tumour.

Rotation speed of the gantry and velocity of leaf movement are both constrained. Maximum rotation speed of the gantry is constrained by the rotation mechanism and the gantry design. The MLC is limited by a number of constraints that influence the maximum speed of leaf movement. Constraints on the MLC are selected to balance beam shape quality and reliably with delivery speed. The constraints on the MLC may include: the total electrical current available to each leaf bank; the total electrical current available in each direction; EMF available to motors; and power output of drives.

To date, the speed of gantry rotation has been relatively slow in comparison to the speed of MLC leaf movement. Therefore, the time-limiting factor of treatment delivery has been gantry speed rotation up to the present.

Improvements and developments in gantry design and rotation mechanisms have increased the attainable gantry rotation speed. That is, the maximum rotation speed of the source around the patient is now higher than in previously known systems. Accordingly, the gantry rotation speed is no longer the time-limiting factor in treatment delivery. In some radiotherapy devices, the gantry is able to rotate between control points faster than the MLC leaves can move to the positions required between control points by the treatment plan. In such devices, if the gantry and MLC are rotated/moved simultaneously at the maximum speed, the gantry will reach the required gantry angle before the MLC leaves reach the position to shape the beam according to the shape of the tumour. For these radiotherapy devices, movement of MLC leaves becomes the time-limiting factor on treatment delivery. These and other factors mean that, in some systems, the movement of MLC leaves is slow compared to the rotation of the radiation source on a gantry such that the movement of the MLC becomes the time-limiting factor in delivering a treatment plan.

The methods of the present disclosure provide means for decreasing treatment delivery time without compromising the quality of beam delimitation. In the present disclosure the arc-segments defined in a treatment plan are ordered to minimise the required movement time for the MLC. In radiotherapy devices with improved gantry design the movement of MLC leaves is the time-limiting factor. Therefore, minimising the required movement of the MLC leaves using the methods described herein can reduce the overall time for completing the treatment plan.

As explained above, a radiotherapy treatment plan comprises: a plurality of beam shapes each at a respective plurality of arc-segments around the patient in order to treat a tumour whilst minimizing radiation dose to healthy tissue. The treatment plan may also comprise gantry rotation velocities and dose rates that combine to deliver the required dose. The beam shape is controlled by a beam limiting device such as a multi-leaf collimator 114.

Figure 2A:
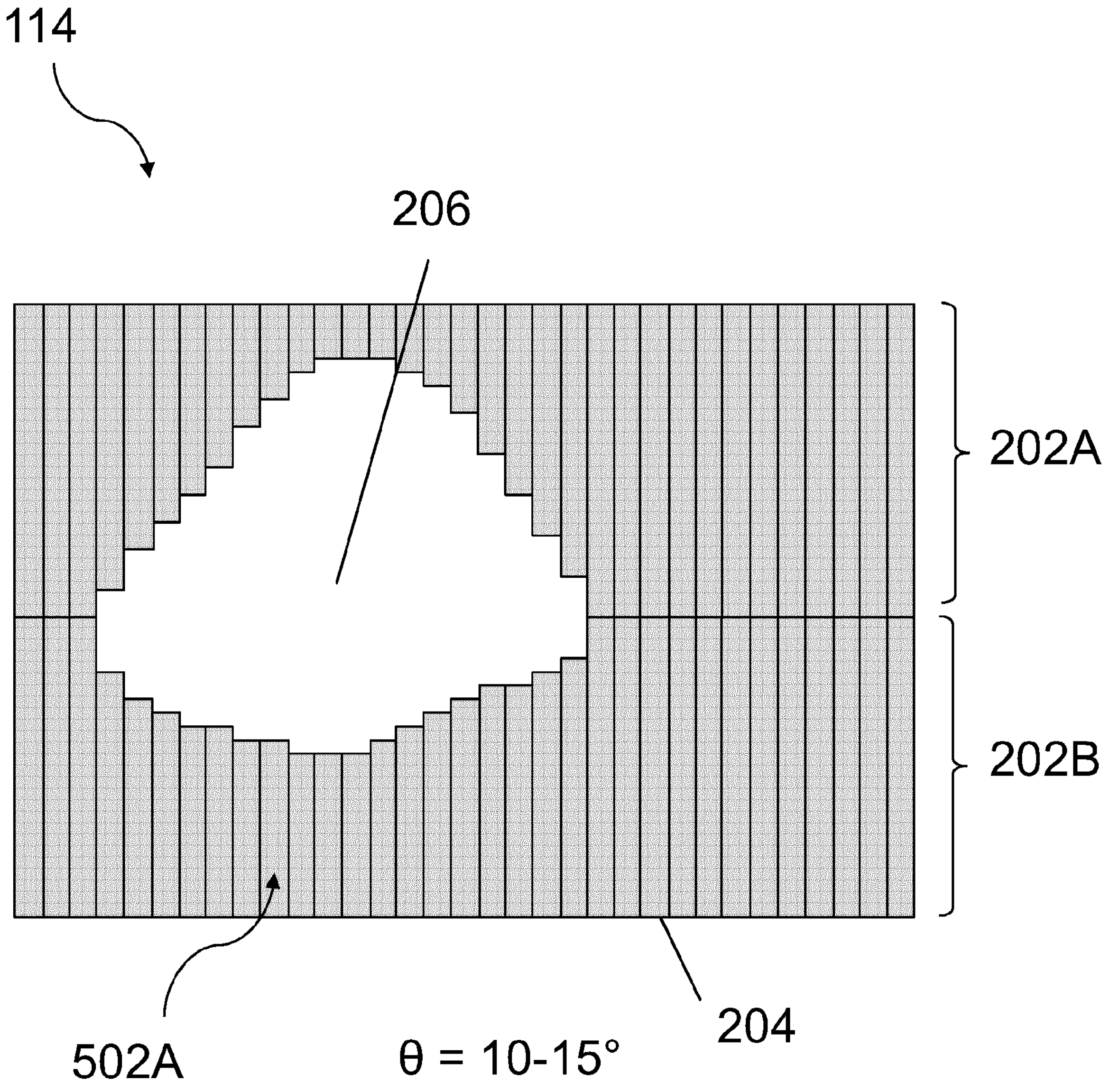
FIGS. 2A, 2B and 2C depict exemplar sets of MLC leaf positions.
Figure 2B:
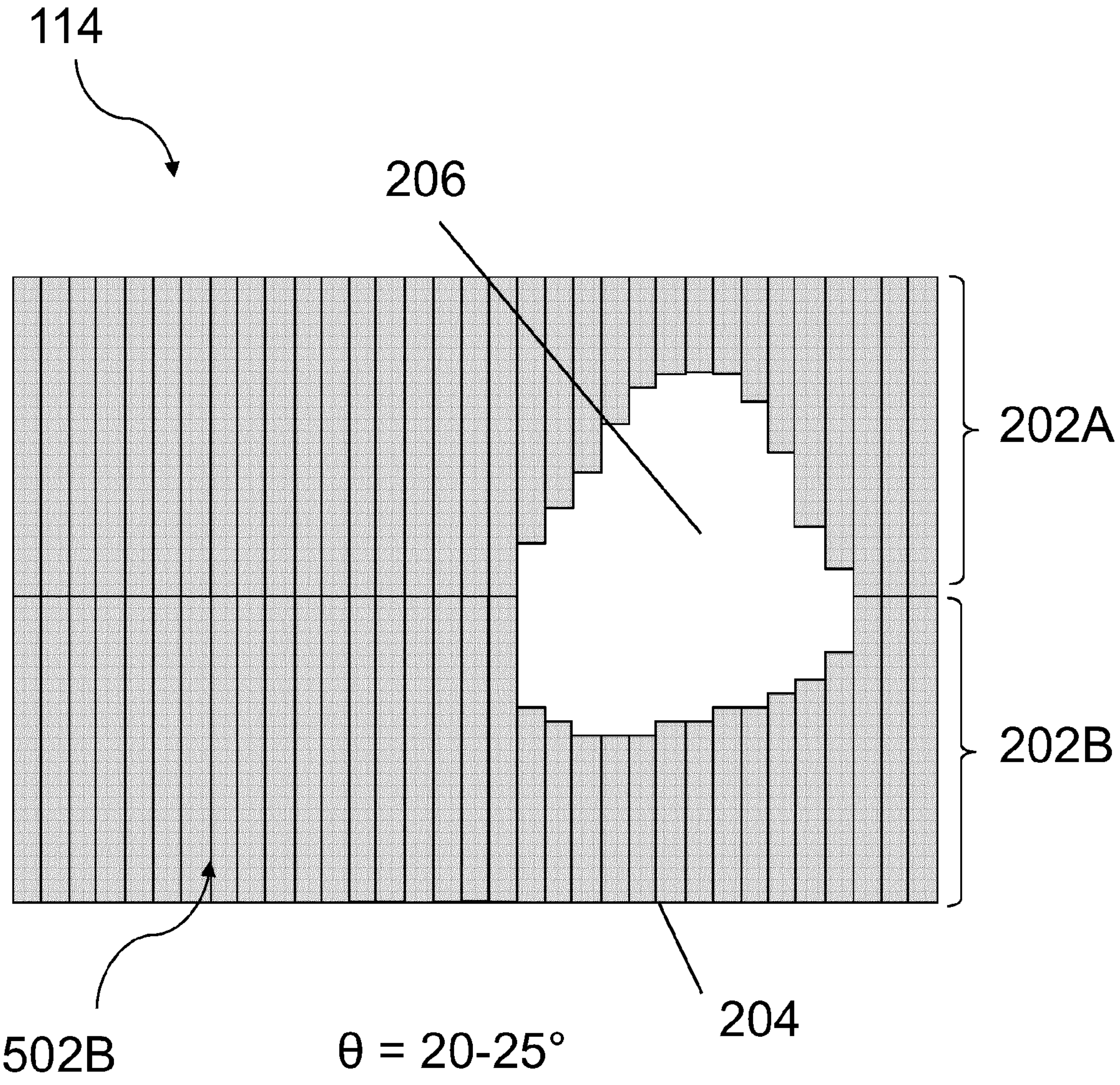
Figure 2C:
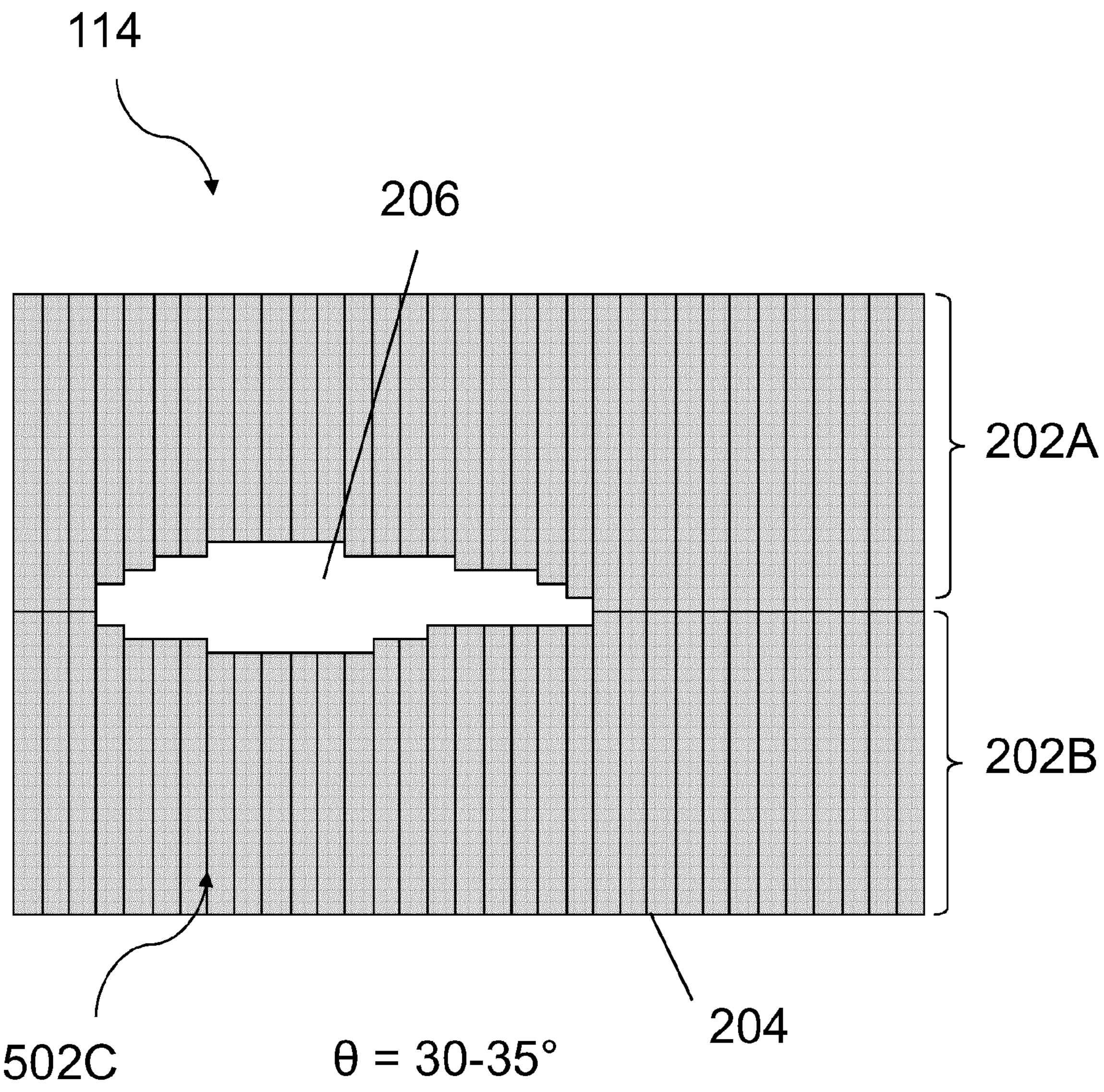

FIGS. 2A to 2C show a multi-leaf collimator (MLC) 114. The multi-leaf collimator includes two leaf banks 202A, 202B, each leaf bank 202A, 202B including a plurality of leaves 204. The leaves 204 are individually moveable longitudinally within the leaf bank 202A, 202B so that they can project into and out of the path of a radiation beam passing through an aperture 206 between the two opposing leaf banks 202A, 202B. The leaves 204 are relatively thin so as to allow a high-resolution aperture shape to be obtained, but they are relatively deep in the direction of the axis of the radiation beam in order to render them sufficiently opaque at X-ray energies. The leaves 204 are relatively elongate (relatively long in the direction perpendicular to their thickness and depth) so as to allow them to adopt a wide range of positions.

Illustrative examples of three different sets of MLC leaf positions are depicted respectively in FIGS. 2A, 2B and 2C. The term 'set of leaf positions' refers to the position of each MLC leaf. Throughout the disclosure the phrase 'MLC shape' is used to refer to the shape of the MLC with each leaf in position according to the 'set of leaf positions'. That is, the terms 'MLC shape' and 'sets of leaf positions' may be used interchangeably. Each of FIGS. 2A, 2B, 2C show a different MLC shape and thus a different aperture shape 206 and will delimit a beam of radiation to the shape of their respective apertures. FIG. 2A depicts a set of MLC leaf positions 502A corresponding to an arc-segment 10-15° (rotation gantry angle range 10-15°) according to a treatment plan 500. The MLC leaf positions 502A define the shape of beam delimitation for the arc-segment θ=10-15°. FIG. 2B depicts a set of MLC leaf positions 502B corresponding to arc-segment 20-25° according to a treatment plan 500. The MLC leaf positions 502B define the shape of beam delimitation for the arc-segment θ=20-25°. FIG. 2C depicts yet another a set of MLC leaf positions 502C corresponding to arc-segment 30-35° according to a treatment plan 500. The MLC leaf positions 502C define the shape of beam delimitation of the arc-segment θ=30-35°. FIG. 2 shows that typically leaves from both banks 202A, 202B are used to form an aperture 206.

The term "arc-segment" refers to a range of gantry rotation angles. An arc-segment may be defined by one or more control points, the one or more control points adjacent in space or angular space. The dose of the treatment delivered in an arc-segment is governed by the velocity of gantry rotation derived in treatment planning from the desired dose distribution. In the illustrative examples of FIGS. 2A, 2B and 2C three different MLC shapes are depicted for three different arc-segments (respectively θ=10-15°, 20-25° and 30-35°). Each arc-segment depicted in FIGS. 2A, 2B and 2C may be defined by one or more control points depending on how the control points are spaced along the complete arc. For instance, if control points are spaced every degree then the arc-segments depicted in FIGS. 2A, 2B and 2C would each be described by 6 control points. In the examples of FIGS. 2A, 2B and 2C the MLC shape does not change in each arc-segment. However, in other examples, small changes to the MLC shape can take place during an arc-segment as long as the MLC leaf speed can keep up with the gantry rotation speed dictated by the treatment plan.

It can therefore be seen that the multi-leaf collimator is used to delimit the beam of radiation into a plurality of different shapes defined in a treatment plan. A set of MLC leaf positions is determined for respective moveable leaves to achieve a given beam shape at each of a plurality of arc-segments.

In one treatment session the MLC is used to define a plurality of beam shapes using a plurality of sets of individual leaf positions, where the leaves move between leaf positions during the treatment session.

Figure 3:
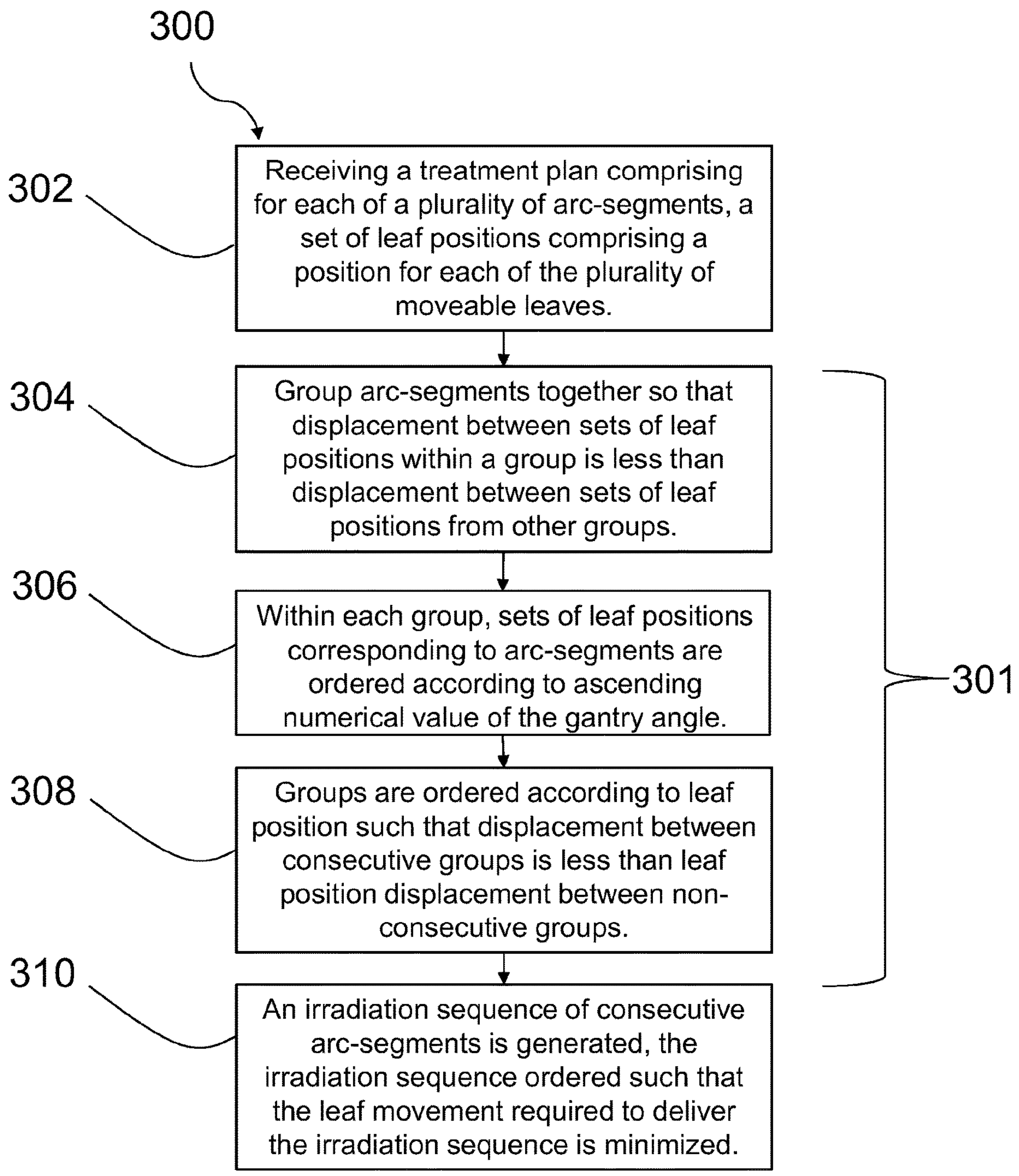
FIG. 3 depicts a method according to the present disclosure.

Reference is now made to the method of the present disclosure, depicted in the flowchart 300 of FIG. 3. Reference is made to an example treatment plan illustrated in FIG. 5.

FIG. 3 illustrates a method 300 according to the present disclosure. The method 300 is performed by a computer, such as a delivery planning computer. The delivery planning computer creates an irradiation sequence based on the treatment plan and the abilities and constraints of the radiotherapy apparatus in question. The irradiation sequence includes ordered multi-leaf collimator positions (MLC shapes) at each of a plurality of arc-segments. As explained above, if the radiotherapy apparatus is constrained by a relatively slow MLC leaf movement speed and a relatively fast gantry rotation speed, then the methods of the present disclosure can reduce delivery time of a treatment plan.

In alternative embodiments the method 300 according to FIG. 3 may be performed at the treatment planning stage, as will be appreciated by the skilled person. The method 300 is performed by a computer, such as a treatment planning computer.

The method is performed by a processor having computer-readable medium which, when executed by the processor, causes the processor to perform the methods disclosed herein. The medium may be a non-transitory computer-readable medium. The term "computer-readable medium" as used herein refers to any medium that stores data and/or instructions for causing a processor to operate in a specific manner. Such storage medium may comprise non-volatile media and/or volatile media. Non-volatile media may include, for example, optical or magnetic disks. Volatile media may include dynamic memory. Exemplary forms of storage medium include, a floppy disk, a flexible disk, a hard disk, a solid-state drive, a magnetic tape, or any other magnetic data storage medium, a CD-ROM, any other optical data storage medium, any physical medium with one or more patterns of holes, a RAM, a PROM, an EPROM, a FLASH-EPROM, NVRAM, and any other memory chip or cartridge.

The method begins from step 302. At step 302, the computer receives a treatmentplan from the treatment planning computer. As explained above, the treatment plan comprises, for each of a plurality of arc-segments, a set of leaf positions (MLC shapes) comprising a position for each of the plurality of moveable leaves. Arc-segments are defined by a range of gantry angles θ, the gantry angles are the angles at which the gantry 104 has rotated with the radiation source 100.

Receiving a treatment plan may include determining the arc-segments and corresponding sets of leaf positions based on a required dose distribution. That is, receiving a treatment plan may include generation of a set of arc-segments at which radiation is to be delivered and a corresponding MLC shape for each arc-segment to achieve the desired beam shape based on anatomical patient data.

In alternative embodiments where the method 300 according to FIG. 3 may be performed at the treatment planning stage, the treatment plan may include an irradiation sequence generated by the method of 300 FIG. 3.

Figure 5:
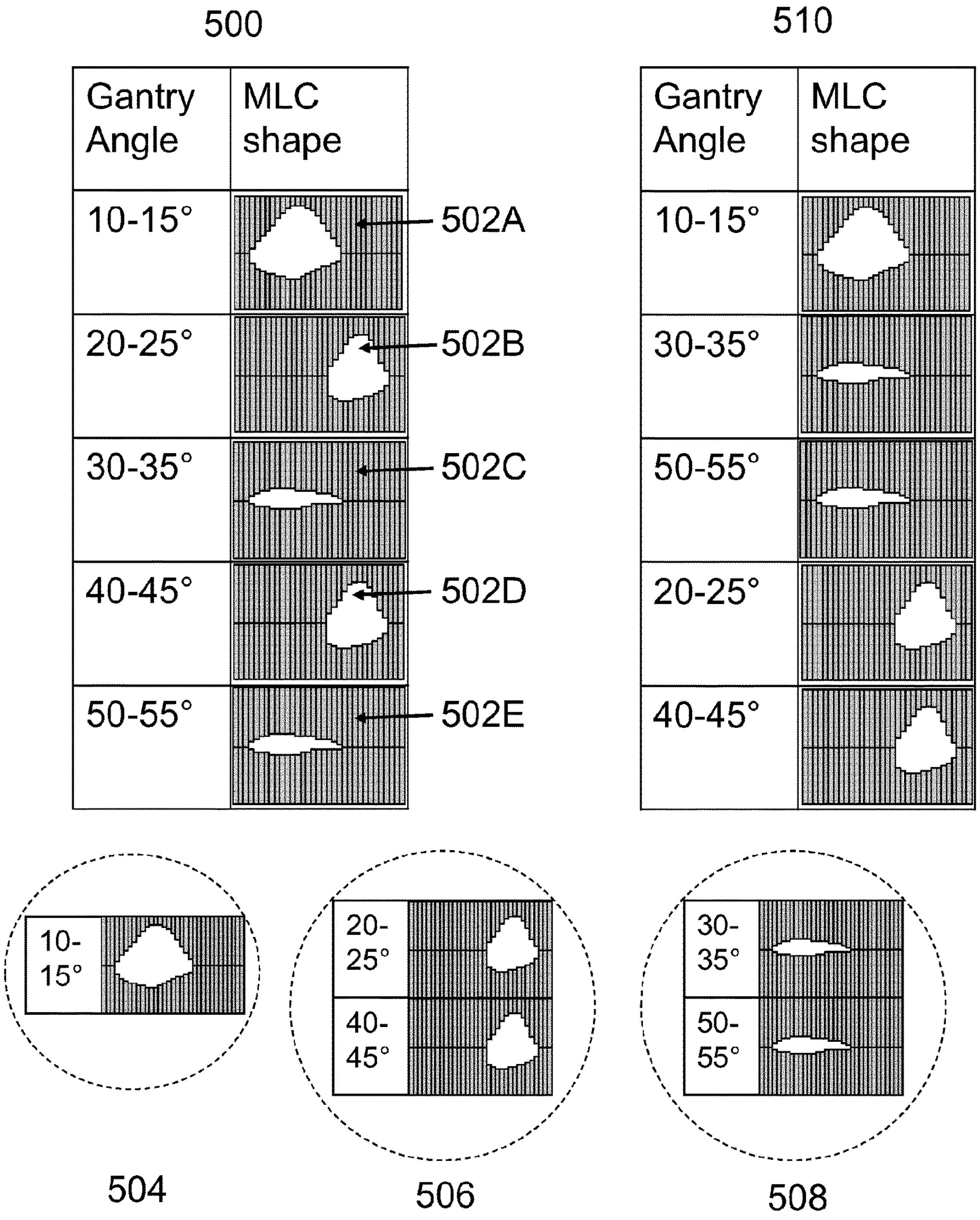
FIG. 5 depicts an illustrative application of the methods according to the present disclosure.

In the illustrative example FIG. 5, a patient treatment plan defines MLC shapes 502A, 502B, 502C, 502D, 502E for five respective arc-segments: θ=10-15°, 20-25°, 30-35°, 40-45°, 50-55°. If the arc-segments are ordered according to ascending numerical value, then an irradiation sequence 500 is formed. That is, irradiation sequence 500 comprises consecutive (sequential) arc-segments that are also contiguous (adjacent/neighbouring in space).

Throughout this disclosure we will use the terms consecutive and sequential to refer to the adjacent angle in the order of delivery. That is, as the treatment plan is delivered, consecutive angles are adjacent in time. Consecutive refers to the order of the angles in the irradiation sequence which is the order the radiation is delivered to the patient. We will use the term contiguous to refer to the adjacent/neighboring angles in space (i.e. the numerical value of the angle).

Known systems deliver a treatment plan in order of contiguous arc-segments, an example of which is irradiation sequence 500. As can be seen, in irradiation sequence 500, the first treatment point is the smallest gantry angle 10-15°. The second treatment point is the next largest gantry angle 20-25°. The third treatment point is the next largest gantry angle 30-35°. The forth treatment point is the next largest gantry angle 40-45°. The fifth and final treatment point is the greatest gantry angle 50-55°. In this way delivering irradiation sequence in known systems involves rotating the gantry in one direction (taken to be clockwise although in some examples may be anti-clockwise) delivering treatment at increasingly large angles of rotation.

Between each treatment arc, the movement between one MLC shape to the next in the sequence may be so great such that the MLC leaves cannot move to the new position fast enough; this is dictated by the speed of the MLC leaves and the speed of gantry rotation. Therefore, in known systems, the gantry has to stop or slow down in order for the MLC leaves to have time to reach the required position for next shape in the sequence. Instances of stopping, starting, speeding up or slowing down the gantry can take valuable time and energy due to the momentum of the gantry. The methods of the present disclosure provide optimised movement of the gantry such that less time is spent adjusting gantry speeds and in many cases the gantry can proceed to move at substantially constant speeds throughout most of the treatment.

The irradiation sequence 500 is generated from a treatment plan and may be considered as part of the treatment plan. It will be understood by the skilled person that components other than those depicted in FIG. 5 may be included in a treatment plan, such as the gantry rotation speed.

At stage 301, after receiving a set of leaf positions for each arc-segment in step 302, the arc-segments are ordered into an irradiation sequence based on the MLC shapes. The arc-segments are ordered to minimize leaf movement time across the delivery sequence. As the gantry rotates treatment is delivered for the next arc-segment in the sequence as it reaches the corresponding angle of rotation.

A specific implementation of this is described below in steps 304 to 308. However, it will be appreciated by the skilled person that other approaches to ordering the arc-segments to minimise leaf movement time are equally as applicable. That is, the following steps form a specific example only.

At step 304, each of the MLC shapes corresponding to arc-segments are grouped into a plurality of groups according to the leaf positions in the MLC shapes. Each MLC shape comprises a set of leaf positions comprising a leaf position for each leaf. That is this step 304 comprises grouping together MLC shapes and the respective arc-segments into one or more groups based on the MLC shapes.

The MLC shapes are grouped such that displacement between leaf positions within a group is less than displacement between leaf positions from other groups. Therefore, a single group will contain similar MLC shapes, each shape always corresponding to a arc-segment. In other words, leaf movement is minimized between MLC shapes within a group.

For an individual leaf, the displacement between two consecutive sets of leaf position (between the leaf position at two consecutive arc-segments) is the absolute distance between the position of the leaf in the first set (at the first arc-segment) and the position of the leaf in the next set (the next arc-segment).

Assuming each leaf is driven at the same speed and all leaves are driven simultaneously, the time taken to move the plurality of leaves between two MLC shapes is defined by the individual leaf with the maximum displacement to move. In other words, the time taken to move the leaves between two MLC shapes is limited by the leaf which has the largest absolute distance to move between shapes. The time taken to move the multi-leaf collimator from a first shape (at the first arc-segment) into a next shape (at the next arc-segment) is equal to the time taken for the individual leaf with maximum displacement to move from its first position into its second position. The individual leaf with the maximum displacement can be considered as the time-limiting factor or the "time-limiting leaf" as the individual leaf limits the time taken for the multi-leaf collimator to move between two MLC shapes. The MLC shapes in question define which leaf in the multi-leaf collimator is the time-limiting leaf.

Minimizing leaf displacement between groups involves identifying the maximum displacement moved by any one leaf (i.e. the time-limiting leaf) between different MLC shapes. The displacement of the time-limiting leaf between its position in a first shape (at a first arc-segment) and its position in second shape (at a second arc-segment) is found. This process is repeated for the first MLC shape with every other MLC shape such that a maximum leaf displacement value is found for each pair combination of MLC shapes. The process is then repeated with every shape such that each shape is compared to every other shape and every pair of shapes has a maximum displacement moved by one leaf (i.e. time-limiting leaf) associated with it.

This allows sets to be grouped together such that displacement is minimized between MLC shapes within a group. Step 304 may comprise grouping the MLC shapes and arc-segments into groups having identical MLC shapes.

A group may contain a single MLC shape corresponding to one arc-segment. Alternatively, a group may contain multiple MLC shapes each corresponding to an arc-segment. In some examples a group may include multiple MLC shapes, the sets of leaf positions being identical (i.e. the sets of leaf positions are the same), each shape nonetheless corresponding to a different arc-segment. In other examples a group may include multiple MLC shapes corresponding to respective arc-segments, the shapes being similar but not identical, but again reducing leaf movement.

In the example FIG. 5, the five MLC shapes 502A, 502B, 502C, 502D, 502E are divided into three groups: 504, 506 and 508. Group 504 contains one shape, 502A, corresponding to arc-segment 10-15°. Group 506 contains two MLC shapes, 502B and 502D, corresponding to arc-segments 20-25° and 40-45° respectively. Group 508 contains two MLC shapes, 502C and 502E, corresponding to arc-segments 30-35° and 50-55° respectively.

Each of the three groups 504, 506, 508 contain MLC shapes which have a smaller displacement of the time-limiting leaf position within the group than between different groups. For example, the displacement of any leaf between 502C and 502E (502C and 502E in the same group) is zero, which is smaller than the displacement of the time-limiting leaf between 502C and 502A (502C and 502A are in a different group). In the illustrative case FIG. 5, the sets of leaf positions within each group are of exactly the same MLC shape. Of course, MLC shapes do not have to be exactly the same to share a group.

Within each group, defined by step 304 or otherwise, the MLC shapes corresponding to arc-segments are ordered into a sequence according to ascending numerical value of the arc-segment in step 306. In other words, the arc-segments are in order of contiguous arc-segments within a group. In the example FIG. 5, group 506 is ordered such that the smallest gantry angle 20-25°(corresponding to MLC shape 502B) is first in the group sequence and is followed by the greatest gantry angle 40-45°(corresponding to MLC shape 502D). Likewise in group 508, the first angle in the group sequence is the smallest gantry angle 30-35°(corresponding to MLC shape 502C) is followed by the greatest gantry angle 50-55°(corresponding to MLC shape 502E). Group 504 contains only one arc-segment 10-15°(corresponding to MLC shape 502A) which renders step 304 unnecessary.

In the example in FIGS. 3 and 5 the arc-segments within the groups are ordered according to ascending numerical value of the arc-segment gantry angle range. In other examples, the arc-segments may be ordered within the group according to descending arc-segment gantry angle. Ordering the arc-segments into ascending order is for the case where the gantry rotation is clockwise (i.e. moves through ascending radiation angles when rotating), ordering the arc-segments into descending order is for the case where the gantry rotation is anti-clockwise (i.e. moves through descending arc-segments when rotating). As will be appreciated by the skilled person, many radiotherapy devices can operate with either clockwise or anticlockwise rotation. However, in a single treatment it is preferable to rotate the source only in one direction (i.e. either clockwise or anti-clockwise) since changing the direction of rotation is difficult due to the momentum of the gantry.

At step 308, all of the plurality of groups, defined by steps 304 and/or 306 or otherwise, are combined into one sequence. The sequence of groups forms an irradiation sequence of the MLC shapes and corresponding arc-segments.

The combination may be such that the most similar groups by maximal leaf positions are consecutive to each other (position difference of the time-limiting leaf). In other words, the maximum leaf position displacement between consecutive groups is less than the maximum leaf position displacement between non-consecutive groups. A first priority for the ordering of groups is with respect to leaf movement, and a second priority given to ordering according to ascending numerical value of the arc-segment gantry angles. For instance in FIG. 5, the group 504 has less leaf displacement required moving to group 508 than to group 506. Therefore, groups 504 and 508 are consecutive when combined into sequence 510 according to step 308. It is therefore clear that the irradiation sequence includes groups 504 and 508 consecutively. The MLC leaf displacement is greater between group 506 and groups 504, than between 504 and 508.

To determine the order consecutive groups appear in the sequence, the arc-segments within the groups are used. The groups are ordered using the first gantry angle within the group (according to step 306, the first arc-segment is the lowest gantry angle in that group). The consecutive groups are ordered according to ascending first arc-segment gantry angle. Since a second priority is given to the numerical order of arc-segment gantry angle, the sequence 510 orders group 504 first, which comprises a minimum gantry angle of 10-15°, followed by group 508, which comprises a minimum gantry angle of 30-35°. Other methods of ordering the consecutive groups to minimize MLC leaf movement and number of complete rotations of the gantry will be appreciated by the skilled person.

The consecutive group(s) and remaining group(s) are ordered to reduce the leaf displacement between the consecutive group(s) and the remaining group(s). In the example in FIG. 5, group 506 can either be ordered before the consecutive groups 504>508 (i.e. before 504) or after the consecutive group 504>508 (i.e., after 508). In some examples this is done to minimise leaf movement. In FIG. 5, the leaf displacement between 506 and 504 is greater than the leaf displacement between 506 and 508, accordingly group 506 is ordered after group 508.

In other examples, different ordering techniques are used to optimise the leaf travel across the course of the irradiation sequence. When ordering the groups, a secondary consideration is to minimise the number of complete rotations required to deliver the sequence. However, it is clear that the primary factor is to minimise the time of leaf movement required to deliver the sequence.

At step 310, by the method of steps 302-308 or otherwise, an irradiation sequence of consecutive arc-segments is generated, the irradiation sequence ordered such that the leaf movement time required to deliver the irradiation sequence is minimized (the time of the time-limiting leaf). In the specific example of FIG. 5, the irradiation sequence is minimized such that maximum leaf displacement between sets of leaf positions corresponding to consecutive arc-segments is less than displacement than between determined sets leaf positions of non-consecutive angles of rotation. Since the displacement of the moveable MLC leaves is directly related to the time taken to move said MLC leaves, then time taken to move the leaves between sets of leaf positions corresponding to consecutive arc-segments is less than time taken to move the leaves between sets of leaf positions corresponding to non-consecutive arc-segments.

The example irradiation sequence 510 shows that there are five consecutive arc-segments which correspond to five MLC shapes. When the method 300 is applied to treatment plan 500, the arc-segments are ordered into the sequence: 10-15°, 30-35°, 50-55°, 20-25°, 40-45° with corresponding MLC leaf position sequence: 502A, 502C, 502E, 502B, 502D.

To deliver the generated irradiation sequence, more than one revolution of the gantry will be required. For example for irradiation sequence 510, at least two revolutions of the gantry are required. On the first revolution, radiation is delivered at arc-segment 10-15° with MLC shape 502A, then the MLC leaves move to MLC shape 502C in order to deliver radiation at arc-segment 30-35°, the MLC leaves remain positions in the shape 502E in order to deliver radiation at arc-segment 50-55°. This assumes that the rotation speed of the gantry allows the MLC time to move between shape 502A and shape 502C, if there is not enough time then another rotation of the gantry will be required. On the second revolution (or the third if required by gantry rotation speed), radiation is delivered at gantry angles 20-25° with MLC shape 502B, then the MLC leaves remain in the same positions for the shape 502D in order to deliver radiation at gantry angles 40-45°. On the first revolution, no radiation is delivered at arc-segments 20-25° and 40-45°, and on the second revolution no radiation is delivered at arc-segments 10-15°, 30-35°, 50-55°. That is, arc-segments can be "skipped" during one or more revolution such that movement of the MLC to the MLC shape for that arc-segment is not required, according to the generated irradiation sequence.

Known systems deliver radiation sequentially such that all control points are delivered in a single revolution and no arc-segments are skipped. For systems with relatively high gantry speed as compared to multi-leaf collimator speed, delivering radiation over more than one revolution can be quicker than delivery over a single revolution due to the speed of gantry movement.

The irradiation sequence 510 is outputted by the computer. In some examples the irradiation sequence is outputted to a control system for controlling a radiotherapy device. In other examples the irradiation sequence is stored in a memory.

The irradiation sequence can be executed by a radiotherapy device such that radiation is delivered according to the treatment plan. The radiotherapy device delivers radiotherapy to a patient at arc-segments in order according to the irradiation sequence. Further details of this are described below in relation to FIG. 4.

Figure 4:
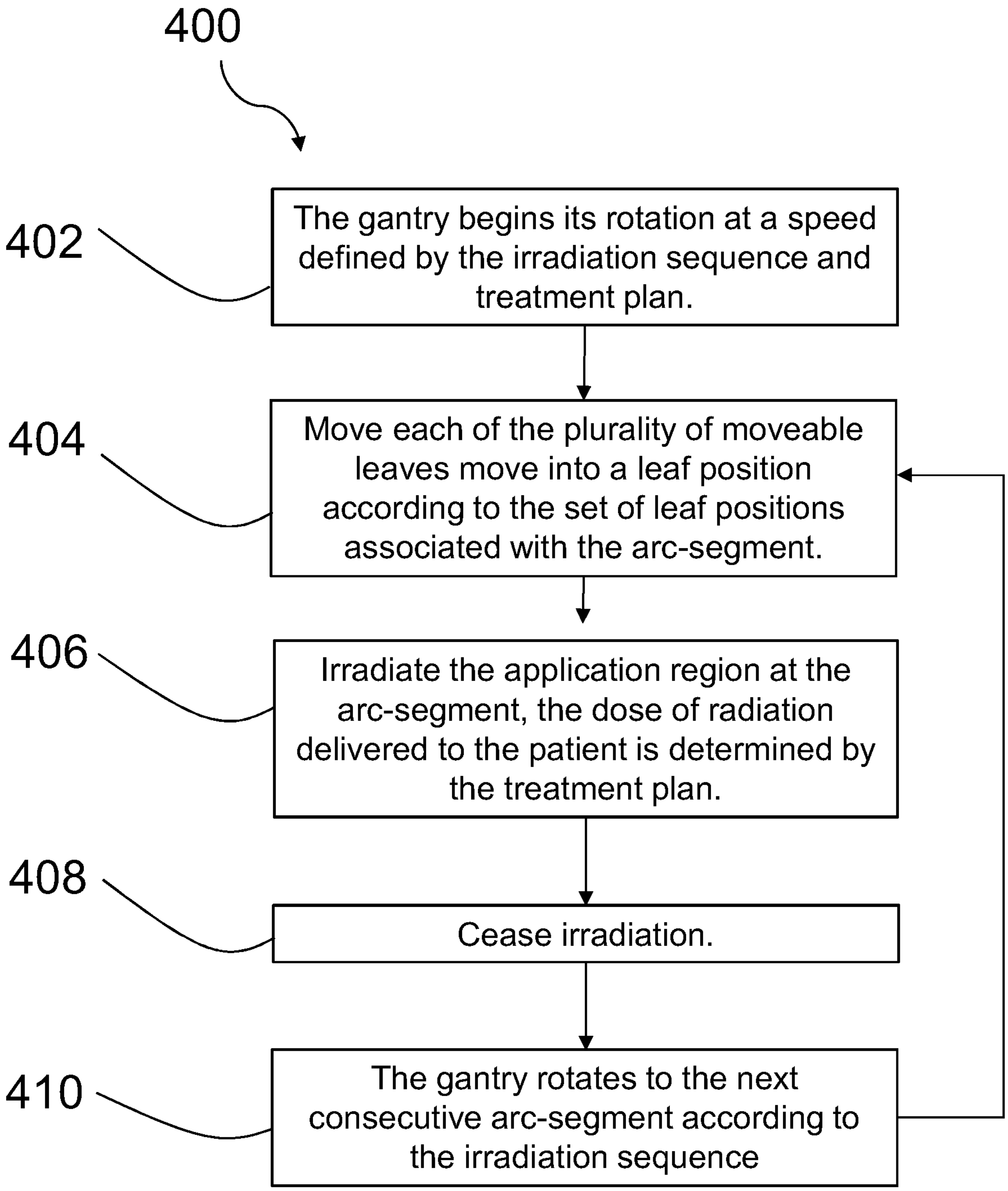
FIG. 4 depicts a method according to the present disclosure.

FIG. 4 illustrates a flowchart 400 which depicts a method of the present disclosure. Reference is made to the example treatment plan illustrated in FIG. 5.

The method 400 is performed by a radiotherapy device 120. The radiotherapy device 120 receives the irradiation sequence from the delivery planning computer, the irradiation sequence defined by method 300. The irradiation sequence includes arc-segments and corresponding MLC shapes which have been discussed in detail but, of course, other information such as component movement velocity and defined doses of radiation for each discrete arc-segment are also provided as will be appreciated by the skilled person.

The method begins from step 402. At step 402, the gantry 104 begins its rotation at a speed defined by the irradiation sequence and treatment plan. The gantry rotation speed remains constant or substantially constant throughout a 360° rotation.

At step 404, the MLC is moved to form the MLC shape associated with the first arc-segment of the irradiation sequence. That is, the position of each of the plurality of moveable leaves is set to delimit the beam of radiation into a particular shape according to the set of leaf positions associated with the first angle of the irradiation sequence. For example, the leaf positions may be controlled to form the positions depicted in FIG. 2A at a first gantry angle of 10-15°(θ=10-15°) according to the irradiation sequence 510.

Steps 402 and 404 occur simultaneously such that the gantry and individual MLC leaves are moving at the same time to reach their respective positions according to the irradiation sequence. For the first gantry rotation, the MLC leaves may move into the first shape before the gantry starts to rotate.

As the gantry 104 rotates the radiation source 100 through the first range of gantry angles according to the irradiation sequence (the MLC shape being correct) the application region of the patient is irradiated in step 406 in a continuous treatment arc. The dose of radiation delivered to the patient is determined gantry rotation speed and is defined by the patient treatment plan. For example, according to irradiation sequence 510, the first radiation dose is delivered over the arc-segment θ=10-15°. Once the radiation dose has been delivered according to the treatment plan for the first arc-segment, the radiation source ceases irradiation of the patient in step 408. The gantry may continue to rotate without a treatment beam present.

At step 410, the gantry continues to rotates to the next arc-segment in the irradiation sequence. The next arc-segment is the next consecutive gantry angles according to the irradiation sequence and not necessarily the next contiguous arc-segment. The next contagious arc-segment may be "skipped" according to the irradiation sequence. The method then returns to step 404. Steps 404-408 are repeated for a next arc-segment in the irradiation sequence. The leaves of the MLC are moved to the set of leaf positions corresponding to the next arc-segment gantry angle at step 404.

Steps 404-410 are repeated for every arc-segment and corresponding set of leaf positions in the irradiation sequence until the treatment has been completed.

Delivering radiation doses according to the treatment plan comprises irradiating the application region at arc-segments from a group followed by irradiating the application region at arc-segments from the other groups. According to the irradiation sequence 510, there are five arc-segments for which steps 402-410 are executed: first 10-15°(leaf positions 502A), followed by 30-35°(leaf positions 502C), 50-55° (leaf positions 502E), 20-25°(leaf positions 502B) and finally 40-45°(leaf positions 502D). In other words, according to irradiation sequence 510, there are three groups for which steps 402-410 would be executed for each group: first group 504, followed by group 508 and finally group 506.

Grouping of Gantry Rotation Velocity

As explained in the methods of FIGS. 3 and 4, a gantry may continuously rotate over multiple revolutions, the treatment delivered according to an irradiation sequence. The irradiation sequence provides an optimized treatment time based on MLC leaf movement speeds, for a radiotherapy machine where the gantry movement speed is relatively fast in comparison to MLC leaf movement speeds. During treatment, time may be spent starting, stopping, slowing down or speeding up the gantry to the correct velocity as defined by dose considerations required by the treatment plan.

The irradiation sequence of the present disclosure may be further optimized by grouping treatment arcs by similar gantry rotation velocity as well as similar MLC leaf position. Similar or the same gantry rotation velocities can be ordered consecutively in the irradiation sequence to reduce overall time spent changing the velocity of the gantry.

In the methods of the present disclosure means to determine an irradiation sequence is determined in which arc-segments are sequentially ordered based on the respective leaf positions. The irradiation sequence is ordered such the displacement required for the leaves over a treatment session is reduced in comparison to known systems and therefore time required to move leaves is also reduced.

A radiotherapy device which has a fast gantry rotation speed in comparison to the MLC leaf movement speed may have leaf movement as the time-limiting factor for patient treatment time. If leaf movement is the time-limiting factor, the methods of the present disclosure are advantageous to reduce the patient treatment time. Decreased patient treatment time can ensure more patients can be treated in a day, increasing throughput of the radiotherapy device, and may shorten patient waiting lists.

The methods of the present disclosure may also enable imaging of the patient to be carried out during treatment, using a technique known as interlacing. Imaging during treatment can assure that patient anatomy is in the correct position. Especially when the grouping of MLC leaves requires radiation to stop in a certain segment to be delivered during next rotation, that time can be used to image the patient. Imaging, such as X-ray imaging, may be disturbed by a radiation treatment. Therefore images should be taken at times a which there is no radiation beam present (i.e. after step 408). The irradiation sequence provided by the methods of the present disclosure can be defined by intervals of time which are either: radiation delivery intervals (intervals of time when a treatment beam of radiation is present) or non-delivery intervals (intervals of time when treatment beam of radiation is not present). Capturing images takes place during the non-delivery intervals so that the radiation of the beam does not interfere with imaging. Interlacing is particularly suited to radiotherapy machines with fast gantry rotation and a grouping of MLC shapes where a beam off is needed at some positions that are to be delivered during next rotation, as in the methods of the present disclosure. As would be appreciated by the skilled person, images may be taken by an imaging device, for example an X-ray tube.

The methods of the present disclosure advantageously require no hardware change of the radiotherapy device in order to implement. The methods may be applied to radiotherapy devices where MLC leaf movement is the time-limiting factor for patient treatment time. Since no hardware alterations are required, the present method can be implemented on existing radiotherapy devices. That is, computer program comprising instructions to implement the method of the present disclosure can be executed by processors of existing radiotherapy devices without requiring any hardware change.

The irradiation sequence 510 shows five arc-segments for illustrative purposes. In practice, a greater number of arc-segments may be used for an irradiation sequence and would likely span a wider range of angles. Depending on the radiation treatment being delivered, any number of arc-segments, range of arc-segments and graduation of arc-segments is possible. In examples the treatment plan includes angles equally spaced 0 through 360 degrees.

The irradiation sequence 510 shows five arc-segments where throughout each arc-segment the MLC does not change position, the MLC remains in one shape. In practice, there may be small changes in MLC position according to the control points of a treatment plan. Control points may be grouped into a continuous arc-segment as long as the MLC leaves can move quickly enough to reach the new position dictated by the control points, which depends on gantry rotation speed.

In some embodiments, instead of the grouping method illustrated in FIG. 300, each of the plurality of sets of MLC leaf positions and corresponding arc-segments are considered separately. In such an embodiment, the irradiation sequence is ordered so that displacement between the sets of leaf positions corresponding to consecutive arc-segments is less than displacement than between determined sets leaf positions of non-consecutive arc-segments. Alternatively, the irradiation sequence is ordered so that time taken to move between the sets of leaf positions corresponding to consecutive arc-segments is less than time taken to move between determined sets leaf positions of non-consecutive arc-segments.

The methods of the present disclosure minimize the displacement of MLC leaf movement in a treatment session. In order to achieve this, a rotation gantry 114 may complete a plurality of revolutions. The rotation gantry 114 may travel solely in one direction (either clockwise or counter-clockwise) in the delivery of one treatment.

In alternative embodiments, a rotation gantry may move in both circular directions within a single treatment session to reach each arc-segment according to the irradiation sequence. A singular directional mode of operation may be preferable since changes in gantry direction may have excessive drive reversal costs to power consumption and time. For a gantry 114 travelling in one circular direction only (either clockwise or counter-clockwise), according to the irradiation sequence 510, a minimum of two revolutions would be needed in order to irradiate at each of the angles in the sequential order. A first revolution would irradiate at angle 10-15°, followed by 30-35°, followed by 50-55°, then a second revolution would irradiate at angle 20-25° and finally 40-45°.

In the methods of the present disclosure, a treatment is described as being delivered according to a plurality of arc-segments with a constantly rotating gantry arm. That is, the radiation source 100 may rotate in a plurality of continuous or substantially continuous treatment arcs. The methods of the present disclosure are also applicable to a treatment delivered at plurality of discrete angles where the gantry pauses to deliver radiation at each discrete angle.

Features of the above aspects can be combined in any suitable manner. It will be understood that the above description is of specific embodiments by way of aspect only and that many modifications and alterations will be within the skilled person's reach and are intended to be covered by the scope of the appendant claims.

The invention claimed is:

1. A method of producing an irradiation sequence for a radiotherapy device to deliver radiation according to a treatment plan, wherein the radiotherapy device comprises a rotation gantry, a radiation source coupled to the rotation gantry for rotation through are segments, and a multi-leaf collimator comprising a plurality of moveable leaves, wherein the multi-leaf collimator is configured to delimit radiation from the radiation source by controlling a position of each leaf of the plurality of moveable leaves, the method comprising:

receiving a treatment plan comprising, for each of a plurality of arc-segments, a set of leaf positions comprising a position for each of the plurality of moveable leaves; and ordering the plurality of arc-segments into an irradiation sequence based on each set of leaf positions, wherein the irradiation sequence, when executed by the radiotherapy device, delivers radiation according to the treatment plan, wherein ordering the plurality of arc-segments into an irradiation sequence comprises:

determining groups of arc-segments in which a maximum displacement between sets of leaf positions corresponding to arc-segments within a group is less than a maximum displacement between sets of leaf positions corresponding to arc-segments from other groups, wherein the irradiation sequence comprises a plurality of groups of angles of irradiation.

2. The method according to claim 1, wherein the plurality of arc-segments are ordered to minimize leaf movement time between consecutive sets of leaf positions.

3. The method according to claim 2, wherein leaf movement time is defined by a maximum displacement for any one leaf of the plurality of moveable leaves to move between sets of leaf positions.

4. The method according to claim 1, wherein the arc-segments in the irradiation sequence are ordered so that the maximum displacement between determined sets of leaf positions corresponding to consecutive arc-segments in the irradiation sequence is less than the maximum displacement between determined sets leaf positions of non-consecutive arc-segments in the irradiation sequence.

5. The method according to claim 1, wherein the arc-segments in the irradiation sequence are ordered so that time taken to move the moveable leaves between sets of leaf positions corresponding to consecutive arc-segments in the irradiation sequence is less than time taken to move the moveable leaves between sets of leaf positions corresponding to non-consecutive arc-segments.

6. The method according to claim 1, wherein the treatment plan defines the sets of leaf positions for respective moveable leaves according to a desired radiation beam shape at each of the plurality of arc-segments.

7. The method according to claim 1, wherein a treatment plan further comprises for each of a plurality of arcs-segments, a set of defined gantry velocities, and wherein the method further comprises:

ordering the plurality of arc-segments into an irradiation sequence based on the set of defined gantry velocities.

8. The method according to claim 1, further comprising:

delivering radiation to an application region according to the treatment plan, wherein delivering radiation according to the treatment plan comprises:

rotating the rotation gantry to position the radiation source according to the ordered arc-segment in the irradiation sequence;

controlling positions of the moveable leaves of the multi-leaf collimator to delimit the radiation at each arc-segment according to the irradiation sequence; and irradiating the application region with radiation from the radiation source.

9. The method according to claim 8, wherein delivering radiation according to the treatment plan comprises:

irradiating the application region at arc-segments from a group then irradiating the application region at arc-segments from one or more other groups.

10. The method according to claim 8, wherein delivering radiation according to the treatment plan comprises:

stopping irradiation from the radiation source between consecutive arc-segments in the irradiation sequence which are non-contiguous angles.

11. The method according to claim 1, wherein the irradiation sequence comprises:

arc-segments ordered such that delivering the irradiation sequence comprises rotating the rotation gantry over a plurality of revolutions.

12. The method according to claim 1, wherein the irradiation sequence includes radiation delivery intervals and non-delivery intervals, and wherein the method further comprises:

capturing one or more images with an imaging device during the non-delivery intervals.

13. A non-transitory computer readable medium comprising computer executable instructions which, when executed by a processor, cause the processor to:

produce an irradiation sequence for a radiotherapy device to deliver radiation according to a treatment plan, wherein the radiotherapy device comprises a rotation gantry, a radiation source coupled to the rotation gantry for rotation through arc segments, and a multi-leaf collimator comprising a plurality of moveable leaves, wherein the multi-leaf collimator is configured to delimit radiation from the radiation source by controlling a position of each leaf of the plurality of moveable leaves, wherein production of the irradiation sequence includes:

receiving a treatment plan comprising, for each of a plurality of arc-segments, a set of leaf positions comprising a position for each of the plurality of moveable leaves; and ordering the plurality of arc-segments into an irradiation sequence based on each set of leaf positions, wherein the irradiation sequence, when executed by the radiotherapy device, delivers radiation according to the treatment plan, wherein ordering the plurality of arc-segments into an irradiation sequence comprises:

determining groups of arc-segments in which a maximum displacement between sets of leaf positions corresponding to arc-segments within a group is less than a maximum displacement between sets of leaf positions corresponding to arc-segments from other groups, wherein the irradiation sequence comprises a plurality of groups of angles of irradiation.

14. A radiotherapy device comprising:

a radiation source for irradiating an application region with radiation;

a rotation gantry configured to rotate the radiation source around the application region through arc segments;

a multi-leaf collimator comprising a plurality of moveable leaves, wherein the multi-leaf collimator is configured to delimit radiation from the radiation source by controlling a position of each leaf of the plurality of moveable leaves according to a treatment;

a processor; and a non-transitory computer readable medium comprising computer executable instructions which, when executed by the processor, cause the device to:

receive a treatment plan comprising, for each of a plurality of arc-segments, determine a set of leaf positions comprising a position for each of the plurality of moveable leaves of the multi-leaf collimator;

order the plurality of arc-segments into an irradiation sequence based on the determined sets of leaf positions of the moveable leaves, wherein the irradiation sequence comprises a plurality of groups of angles of irradiation; and deliver radiation to an application region according to the irradiation plan, wherein to deliver radiation according to the irradiation plan, the instructions cause the device to:

rotate the rotation gantry to position the radiation source according to the ordered angles in the irradiation sequence;

control the positions of the moveable leaves of the multi-leaf collimator to delimit the radiation at each arc-segment according to the treatment plan; and irradiate the application region with radiation from the radiation source, wherein ordering the plurality of arc-segments into an irradiation sequence comprises:

determining groups of arc-segments in which a maximum displacement between sets of leaf positions corresponding to arc-segments within a group is less than a maximum displacement between sets of leaf positions corresponding to arc-segments from other groups, wherein the irradiation sequence comprises a plurality of groups of angles of irradiation.

* * * * *